United States Patent [19]

Smith, Jr. et al.

[11] 4,424,444
[45] Jan. 3, 1984

[54] METHOD FOR SIMULTANEOUS MEASUREMENT OF BOREHOLE AND FORMATION NEUTRON LIFETIMES

[75] Inventors: Harry D. Smith, Jr.; Dan M. Arnold, both of Houston, Tex.

[73] Assignee: Halliburton Company, Duncan, Okla.

[21] Appl. No.: 394,219

[22] Filed: Jul. 1, 1982

Related U.S. Application Data

[63] Continuation of Ser. No. 182,171, Aug. 28, 1980, abandoned.

[51] Int. Cl.³ .............................................. G01V 5/00
[52] U.S. Cl. .................................... 250/270; 250/262
[58] Field of Search ............... 250/262, 264, 265, 269, 250/270

[56] References Cited

U.S. PATENT DOCUMENTS

| | | | |
|---|---|---|---|
| 3,930,153 | 12/1975 | Scott | 250/270 X |
| 4,122,338 | 10/1978 | Smith, Jr. et al. | 250/270 X |
| 4,152,590 | 5/1979 | Smith, Jr. et al. | 250/270 X |
| 4,157,469 | 6/1979 | Randall | 250/270 X |
| 4,223,218 | 9/1980 | Jacobson | 250/269 X |
| 4,315,148 | 2/1982 | Randall | 250/270 X |

*Primary Examiner*—Davis L. Willis
*Attorney, Agent, or Firm*—William J. Beard

[57] ABSTRACT

The present invention concerns methods for measuring simultaneously the formation and borehole components of thermal neutron lifetime as decay time. The borehole and formation are irradiated with pulsed 14 MEV neutrons. During the interval between neutron pulses the capture gamma radiation is measured in at least four, non-overlapping, contiguous time gates. A background radiation measurement is also periodically made. The background corrected capture gamma radiation measurements are combined to derive simultaneously, the formation and borehole neutron lifetime components which are then recorded as a function of borehole depth.

21 Claims, 7 Drawing Figures

METHOD FOR SIMULTANEOUS MEASUREMENT OF BOREHOLE AND FORMATION NEUTRON LIFETIMES

This application is a continuation of copending application Ser. No. 182,171 filed Aug. 28, 1980 now abandoned.

BACKGROUND OF THE INVENTION

This invention relates to in situ measurements of earth formations traversed by a well borehole. More particularly, the invention relates to the measurement of the thermal neutron decay time (or neutron lifetime) of earth formations in the vicinity of a wellbore.

The observed decay rate of the thermal neutron population in the vicinity of a well borehole following a pulse or burst of high energy neutrons can be approximated by the sum of formation and borehole exponential terms plus a background term which can vary according to formation and borehole conditions. In typical field conditions the borehole component of the thermal neutron lifetime, or decay time, decays more rapidly than the formation component of thermal neutron lifetime. The primary parameter of interest is $\tau_F$, the mean lifetime of thermal neutrons within the formation. Another parameter of interest is $\tau_B$, the mean lifetime of thermal neutrons in the borehole. The present invention provides methods and apparatus for determining both of these parameters of interest simultaneously.

The system and methods of the present invention employ a pulsed source of fast neutrons. The fast neutrons are slowed down (or moderated) to thermal energy rapidly by interaction with the nuclei of the elements in the borehole, the earth formations surrounding the borehole, and fluids contained in the pore spaces of such formations. The thermal neutron lifetime or decay time of the earth formation is largely determined by the salt or chlorine content of the earth formations. The hydrogeneous matter in the pore spaces and borehole rapidly attenuates or slows down the fast neutron flux emitted by a source of pulsed fast neutrons. The fast neutrons when slowed to thermal energy are said to be thermalized and may then be captured by the nuclei of elements comprising the formation matrix and fluids filling the formation matrix and the materials comprising the wellbore, including the borehole fluid, logging instrument, and possibly well casing. The element chlorine, which is found in highly saline borehole fluids and earth formation fluids in the pore spaces of earth formations in the vicinity of a borehole when a high salt (NaCl) content is present, has a very high capture cross-section for thermalized neutrons. Thus a measurement of the thermal neutron decay time or neutron lifetime of earth formations in the vicinity of a well borehole can be indicative of the amount of saline fluids present in the pore spaces of the formation. When combined with formation water salinity, porosity measurements and measurements of formation shaliness, this results in a combination which can be used to discriminate oil from salt water filled pore spaces in the vicinity of a well borehole.

BRIEF DESCRIPTION OF THE PRIOR ART

Two commercially available services for measuring the thermal neutron lifetime or thermal neutron decay time of earth formations in the vicinity of a well borehole are presently available. Both of these commercial techniques employ the assumption that the wellbore materials are of a significantly higher thermal neutron capture cross section than the surrounding earth formations. By making this assumption, then a neutron burst or pulse may be emitted from a well logging instrument situated in the borehole, and after a time delay which is sufficient to allow the thermal neutrons in the well borehole itself to all be substantially captured by the wellbore nuclei having a high capture cross-section, the borehole decay time component may be ignored. Then measurements of the rate of decay of the thermal neutron population in the earth formations may be measured. These commerical neutron lifetime (or thermal neutron decay time) measurements have proven to be particularly valuable in evaluating the producing potential of earth formations in the vicinity of cased well boreholes. In both of these presently available commercial techniques, a well logging instrument which traverses the wellbore uses a pulsed source of high energy (14 Mev) neutrons, usually produced in a deuterium-tritium accelerator tube.

The first commercially available technique, at the present time is known as the "fixed gate" technique. In this technique, the neutron source is repetitively pulsed and for each neutron pulse a cloud of fast neutrons is injected in a generally spherically symmetric fashion about the source into the surrounding earth formations. The fast neutron cloud passes from the well tool through the drilling mud, wellbore casing, cement between the casing and the earth formation surrounding the wellbore and into the earth formations. In this technique, typically each such pulse of fast neutrons has approximately a constant intensity and lasts typically for a time duration of from 20 to 50 microseconds. The number of thermal neutrons comprising this cloud or population then decays exponentially due to the capture of the thermalized neutrons by nuclei in the earth formations and borehole.

After an initial time period following the neutron burst (typically about 300–400 microseconds), during which the resultant capture gamma ray distribution in the borehole, mud and casing is assumed to be substantially dissipated, measurements of the number of thermalized neutrons in the vicinity of the well tool are made during two successive time intervals or gates, of fixed duration. These two measurements made during the constant time gates or successive time intervals can then be used to define an approximately exponential decay curve for the thermal neutron population in the earth formation surrounding the borehole.

The assumption is made that enough time has passed following the neutron burst for essentially all thermalized neutrons in the vicinity of the wellbore itself to have been captured by the borehole elemental nuclei. The assumption is that the borehole component of the thermal neutron decay or thermal neutron lifetime is generally shorter than the earth formation component of thermal neutron decay or thermal neutron lifetime. This usually occurs when borehole drilling fluids having a high chlorine or salt water content are encountered. However, in boreholes containing air, gas, fresh water or oil this relationship does not always hold. Accordingly, one particular advantage of the present invention over this "fixed gate" prior art thermal neutron lifetime measuring technique is that no assumption is made as to the relative thermal neutron decay time characteristics of the borehole fluid with respect to the thermal neutron decay time or lifetime characteristics of the earth formations surrounding the borehole.

The thermal neutron population in the formation in the vicinity of the borehole is inferentially measured during the two fixed time gating intervals following each neutron burst or pulse by measuring the capture gamma rays resulting from the capture of thermalized neutrons by the nuclei of materials comprising the earth formations and fluids in the pore spaces therein. The two time intervals or gates most frequently used, for example, in the fixed gate technique for measuring thermal neutron decay times can occur between 400–600 microseconds following the neutron burst and between 700–900 microseconds following the neutron burst. These values are used in typical earth formations regardless of the salinity of the fluid present in the borehole. Since these fixed time gates are designed for general borehole use regardless of salinity they are not optimized as to maximizing count rate. Because the gates are delayed for a relatively long time after the burst, the count rate during the gates is lower than optimum in saline fluid filled boreholes. This can lead to statistical uncertainty in the measurement of $\Sigma$.

If neutron diffusion effects are ignored, the relationship for the decay of a thermal neutron population in a homogeneous medium having a thermal neutron macroscopic capture cross-section $\Sigma$ can be expressed as in Equation 1.

$$N_2 = N_1 e^{-\Sigma(vt)} \qquad (1)$$

wherein $N_1$ is the number of thermal neutrons at a first point in time $t_1$; $N_2$ is the number of thermal neutrons present at a later point in $t_2$; e is the Naperian logarithim base; t is the time between two measurements $(t_2-t_1)$; and v is the velocity of the thermal neutrons. The macroscopic thermal neutron capture cross section $\Sigma$ of a reservoir rock (which can be obtained from Equation 1) is dependent upon its porosity, matrix composition, shaliness, the formation water salinity, and the quantity and type of petroleum contained in the pore spaces therein. This quantity thus represents a valuable physical parameter or measurement of the formation to be obtained.

The second presently commercially available prior art technique for measuring thermal neutron decay time or thermal neutron lifetime uses a reciprocal relationship of the macroscopic thermal neutron capture crosssection $\Sigma$ which is defined in terms of $\tau$ the time constant for absorption of the thermal neutrons. A relationship analogous to Equation 1 but defined in terms of $\tau$ is given by:

$$N = N_o e^{-t/\tau} \qquad (2)$$

where $\tau = 1/v\Sigma$. In Equation 2, N represents the thermal neutron density at any time t; $N_o$ is the thermal neutron density at an initial time, $t_o$; e again represents the Naperian logarithm base constant; and $\tau$ is the time required for the thermal neutron population to decay 1/e of its value at $t_o$.

In measuring the thermal neutron decay time using the second prior art technique known as the "sliding gate" arrangement, the well logging instrument emits a pulse or burst of fast neutrons into the formation the duration of which is actually controlled and related to previously measured values of $\tau$ of the earth formations. For example, the neutron pulse duration may be one $\tau$ duration. Gamma ray detectors are used to obtain counts of capture gamma rays during two successive time intervals following the generation of the neutron cloud in the vicinity of the well borehole in order to define the exponential decay curve. In this technique, however, the two intervals used for measuring the gamma ray population to define the exponential decay curve are not fixed in duration or in starting time following the neutron burst. The value of $\tau$ previously measured on the previous neutron burst cycle is used to establish the neutron burst duration for the generation of the fast neutrons as well as the waiting interval to the opening of the first time gate following the burst, the duration of the first time gate, the duration of the second time gate and the waiting interval between the initiation of the first and second time gates. All of these times are adjusted until a predetermined relationship to $\tau$ is satisfied. For example, the second measurement gate duration may be two $\tau$ in duration. A waiting interval of two $\tau$ following the neutron burst maybe used before the opening of the first gate. The first gate may have a duration of one $\tau$.

In both of the above described prior art systems for determining thermal neutron lifetime or decay time, the neutron source and one detector are all that is essential for the measurement. However, in both of the commercially available techniques, dual spaced detectors are employed and measurements at the detectors of the capture gamma radiation due to thermal neutrons are used to generate approximations or measurements of the porosity of the earth formations in the vicinity of the borehole. The system of the present invention also employs two detectors and can make porosity measurements.

As previously discussed, both of the commercially available techniques for measuring thermal neutron decay time at present employ the assumption that the borehole thermal neutron decay time is substantially less than that of the earth formations in the vicinity of the borehole and may thus be discriminated against by "timing out" the borehole component. In the sliding gate techniques at a time interval substantially following both of the detection gates used for $\tau$ or $\Sigma$ measurements, a background time gate can be used to measure the background of gamma radiation due to thermal neutron capture events in the borehole and earth formations surrounding the wellbore. These background counts are, after appropriate normalization, generally subtracted from the counts made during the two measurement gates in such a system so as to remove the influence of natural gamma ray background which occurs in the vicinity of the well borehole and any background which may be induced within the gamma ray detectors and formation by the neutron source. It should be noted that both of the previously described commercial well logging systems do not use all of the possibly available gamma ray count information following each burst of neutrons. The time intervals during which the detectors are not gated to accept information are lost in both these prior art systems. Thus, the full utilization of the neutron output from the neutron generator is not made in the prior art schemes. Similarly, both of the prior art techniques assume that the formation thermal neutron lifetime or thermal neutron decay time may be essentially completely separated from that of the borehole component by time gating. Even under ideal conditions, this assumption is not completely valid. The present invention utilizes techniques and systems which avoid each of these prior art assumptions and limitations.

BRIEF DESCRIPTION OF THE INVENTION

In the present invention a well logging tool is moved through the borehole and includes a pulsed source of fast neutrons and two radiation detectors. The neutron source generates a pulse of fast neutrons of approximately constant intensity for a duration of between 10 and 30 microseconds. These neutrons are introduced into the media comprising the well borehole and surrounding formations and result in a thermal neutron population being generated from the slowing down of the fast neutrons in the earth formation media and the borehole. After a very shoft pause to allow moderation of the fast neutrons following the neutron pulse, the detectors are gated on and the capture gamma radiation resulting from the capture of thermal neutrons in the borehole and earth formations in the vicinity of the borehole are recorded essentially continuously until the next neutron burst is about to begin. During multiple time gates which occur during this essentially continuous interval, the capture gamma ray counting rate is observed in six or more essentially contiguous time gates. The multiple time gate measurements of the counting rates are supplied to a thermal neutron lifetime computer which computes the formation and borehole neutron lifetime components by means of least squares fitting of this count rate data taken during six, or more, essentially contiguous time gates following each neutron burst. The thermal neutron lifetime computer is enabled to calculate both the borehole thermal neutron lifetime component and the earth formation thermal neutron lifetime component, simultaneously. Approximately once per second, and for approximately five percent of the one second operating cycle, the neutron source is turned off and the detectors are used to establish any relatively long lived background counting rate due to source neutron induced gamma ray activity within the gamma ray detector, the formation, borehold, logging sonde, or natural gamma radiation in the vicinity of the borehole. This background gamma ray information is then properly normalized and subtracted from the six or more time gate measurements of thermal neutron capture gamma rays made following each neutron burst.

Electronic systems are provided in the downhole tool and at the surface for producing the measurement sequence and neutron pulses as described. Additionally, synchronization or sync pulses are also generated to provide a means for separating the counts of gamma rays representative of thermal neutron capture during each of the six or more gating portions of the measurement cycle, as previously described. Moreover, a surface computer for deriving the thermal neutron decay times, or lifetimes, of the borehole component and earth formation components is provided and is attached to a well logging recorder in which a record medium may be moved as a function of borehole depth, while the logging instrument is moved through the borehole. The formation and borehole components of thermal neutron lifetime may be plotted as a function of borehole depth on this recorder. Thus, the system of the present invention includes techniques for determining the value of thermal neutron decay or macroscopic thermal neutron capture cross-section of the borehole and the surrounding media simultaneously.

The invention is best understood by reference to the following detailed description thereof when taken in conjunction with the accompanying drawings, in which:

DESCRIPTION OF THE PREFERRED EMBODIMENTS

Figure 1:
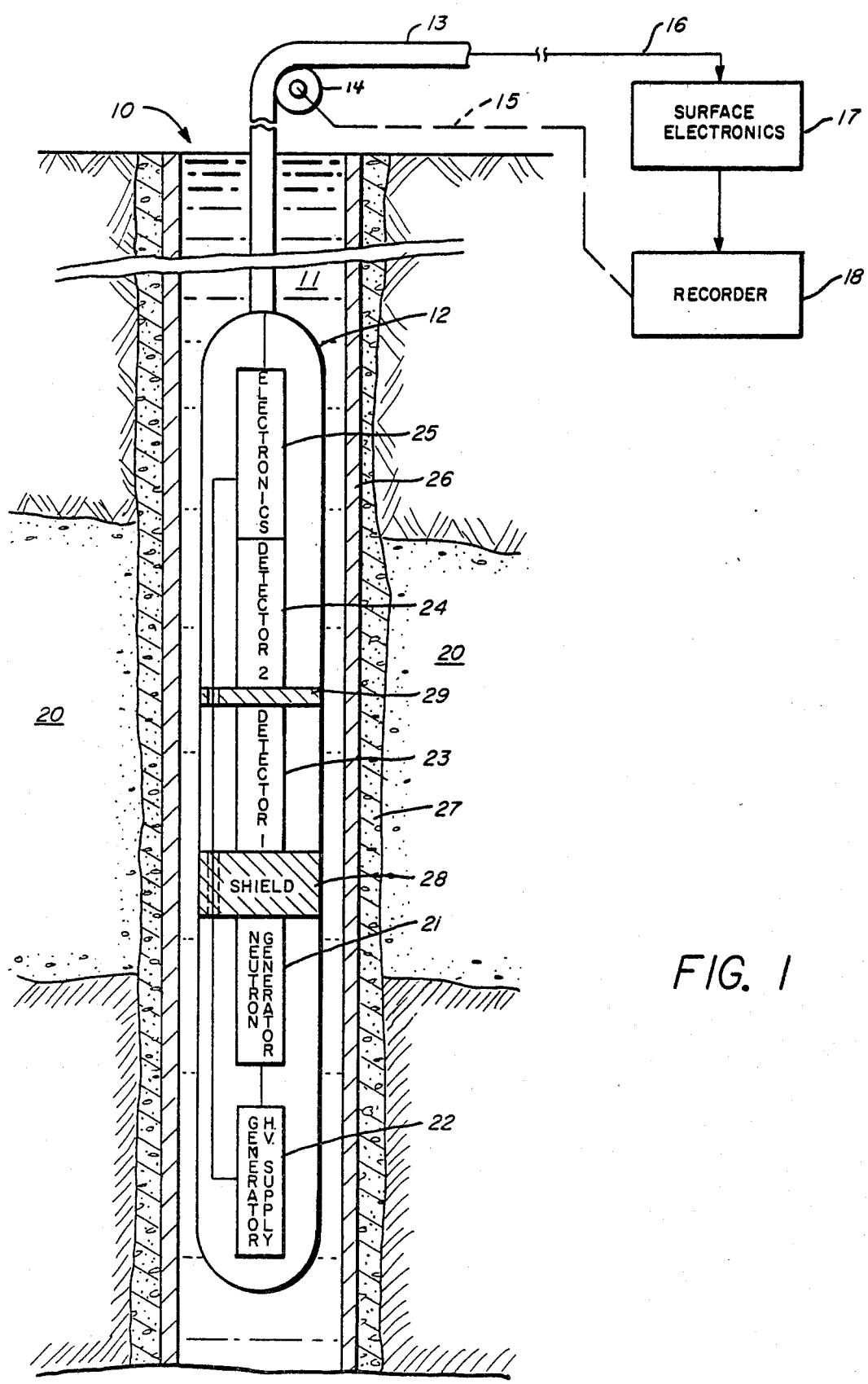
FIG. 1 is a schematic drawing showing a well logging system in accordance with the present invention.

The previously discussed prior art techniques for determining thermal neutron lifetime or decay time can encounter two major problems. these two major problems are: (1) Under certain formation and borehole conditions, the borehole component has not decayed to a negligible level prior to the beginning of the gating of detectors sequence for determining the neutron lifetime. This results in an erroneous measurement of $\tau_F$, and; (2) The statistical accuracy of $\tau_F$ is sometimes quite poor because the decay rate samples have to be taken at relatively long intervals of time after the neutron burst in order to minimize the effects of the borehole component.

A third problem in prior art neutron lifetime logging techniques was first discussed by Mills, et al in a paper entitled "Pulsed Neutron Experiments in a Borehole Model", Mills, et al in Nuclear Science and Engineering, Vol. 21, Pages 346–356 (1965). The Mills, et al paper shows that even if $\tau_F$ is computed from count rate data taken at time delays sufficient for the borehole component to decay to a negligible level, that the computed $\tau_F$ is still a function of $\tau_B$, the lifetime of thermal neutrons within the borehole. This may be thought of as being due to thermalized neutrons continuously diffusing back into the borehole from the formation even after the "original" borehole thermal neutron population has decayed by capture to a low level. Thus, the two prior art techniques completely dismiss the effect caused by this third problem. The present invention however takes into account the problems of all three effects and results in a much more reliable measurement of the thermal neutron lifetime or decay time than heretofore has been available.

In order to obtain accurate hydrocarbon saturations from pulsed neutron lifetime or decay time logs. The following three criteria should be met:

(1) $\tau_F$, the observed lifetime of the formation component, should be computed from count rate data which contains no contributions from neutron capture within the borehole;

(2) $\tau_F$ should be statistically as accurate as possible; and (3) The intrinsic mean lifetime of the formation component $\tau_{Fi}$ should be determined before hydrocarbon saturation calculations are made.

According to the previously mentioned Mills, et al paper, the measured lifetime can be related to $\tau_{Fi}$, the intrinsic lifetime only if $\tau_B$ is known. It is therefore, desirable to measure both the formation component $\tau_F$ and the borehole component $\tau_B$ of the thermal neutron lifetime or decay time simultaneously for maximum accuracy.

As previously discussed, the observed decay rate of the thermal neutron population in the vicinity of a well borehole following a burst of high energy neutrons may be described as the sum of a formation component, a borehole component and a background component. This may be expressed mathematically as in Equation 3.

$$C(t) = Ae^{-t/\tau_B} + Be^{-t/\tau_F} + C_B \quad (3)$$

Figure 3:
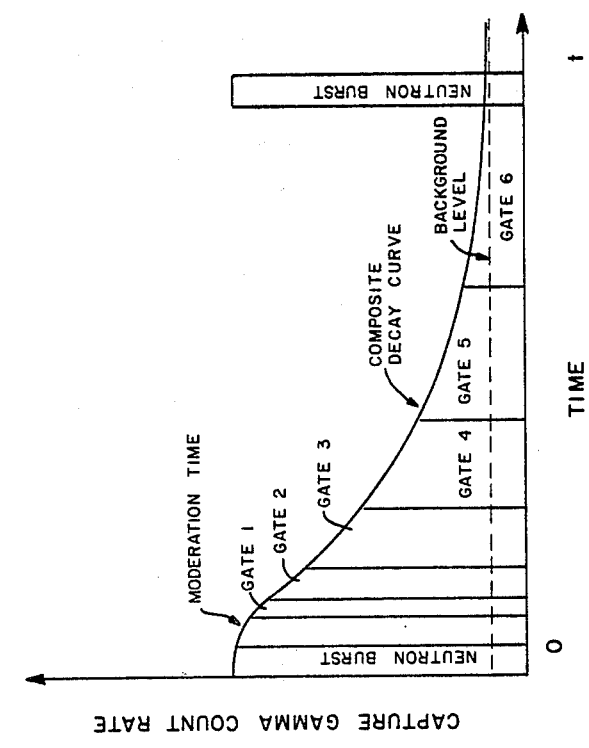
FIG. 3 is a graphical relationship illustrative the composite thermal neutron population decay curve and time gates according to one embodiment of the present invention.

In Equation 3, C(t) is the counting rate at any time t measured ffrom a reference time. A and B are constants which may be interpreted according to FIG. 3 of the drawings with A representing the initial borehole component at the reference time=0, and B representing the initial formation component at the reference time=0. These components are shown in FIG. 3 as intercepts on the ordinate axis as a function of time. $\tau_B$ in Equation 3 represents the borehole component of composite lifetime of thermal neutrons. $\tau_B$ may be thought of as the slope of the borehole component curve of FIG. 3. Similarly, $\tau_F$ represents the formation lifetime component of the composite neutron lifetime and may be thought of as the slope of the formation component curve of FIG. 3. Finally, $C_B$ represents the component of the count rate due to the long lived radiation and may be thought of as a constant component as shown by the horizontal line labelled background in FIG. 3. The composite thermal neutron decay curve shown in FIG. 3 is the resultant or summation of the borehole component, formation component and background component curves illustrated therein.

Figure 4:
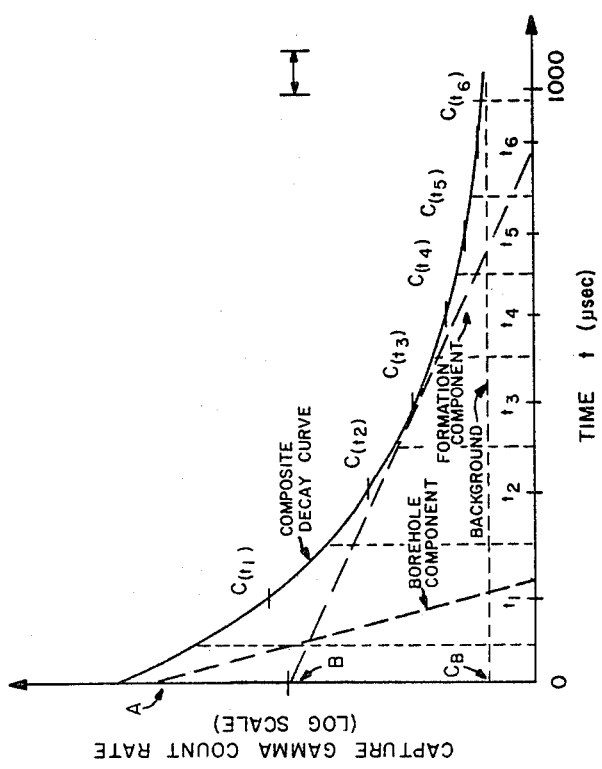
FIG. 4 is a schematic graphical illustrating a telemetry sequence as a function of time in the present invention.

In the technique of the present invention, the background component $C_B$ is measured during a separate portion of the operating cycle as illustrated in FIG. 4. Referring now to FIG. 4, a telemetry stream from a downhole instrument which will be described in more detail subsequently is shown as a function of time. A synchronization pulse begins each operating cycle of the downhole instrumentation. This synchronization pulse is followed immediately by a neutron burst of approximately constant intensity and having a duration which will be described in more detail subsequently. Six or more time gating intervals follow each neutron burst during which count rate measurements at a detector spaced from the source are made and transmitted to the surface. The multiple time gating intervals are essentially contiguous and last for a total of approximately 1 millisecond following the synchronization pulse. This repetitive operating cycle is repeated approximately 1000 times during a one second interval. At the end of a 945 millisecond interval, a background gate shown in FIG. 4 is used to count background radiation corresponding to $C_B$ in FIG. 3. During this 55,000 microseconds or 55 milliseconds interval, the neutron generator is not pulsed. Therefore, the measurements made during this time interval, after approximately 5 milliseconds to allow thermal capture radiation following the last sequential neutron burst to develop to a negligible level, will contain only count information due to radiation attributable to background. This background count information is telemetered to the surface by the downhole system and processed as will be described in more detail subsequently.

When the background counting rate $C_B$ is measured in the manner described and telemetered to the surface, it may be subtracted from the composite counting rate C(t) of Equation 3 to obtain a net counting rate C'(t) as given in Equation 4.

$$C'(t) = C(t) - C_B = Ae^{-t/\tau_B} + Be^{-t/\tau_F} \quad (4)$$

In Equation 4, the symbols are all as previously defined.

In the method of the present invention, as illustrated with respect to FIGS. 3 and 4, six (or more) counting rates measured in the six time gates following the neutron burst and labelled $T_1$, $T_2$, $T_3$, $T_4$, $T_5$, and $T_6$ are combined by a least-squares fitting technique. The counting rate measurements in the six time gates may be fitted in real time in a surface computer, for example, in order to obtain the parameters of interest in Equations 3 and 4. The fitting procedures yield $\tau_F$, $\tau_B$, A and B as previously defined. It will be observed that the six (or more) approximately contiguous time gating intervals illustrated in FIG. 3, have negligible or minimal time delay between each gate. Therefore, the full counting rate information (following a short moderation time interval) from the end of the neutron burst to the opening of the first time gate which moderation time is typically of the order of 20–30 microseconds is utilized in the method of the present invention. No count information is lost due to waiting for a borehole component to decay. Additionally, since this technique simultaneously determines $\tau_F$ and $\tau_B$, the criterion of the Mills, et al paper previously referenced is met.

Figure 5:
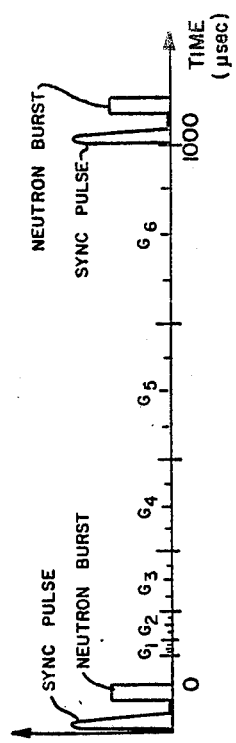
FIG. 5 is a graphical relationship illustrating the composite thermal neutron population decay curve and time gates according to a second embodiment of the present invention.
Figure 6:
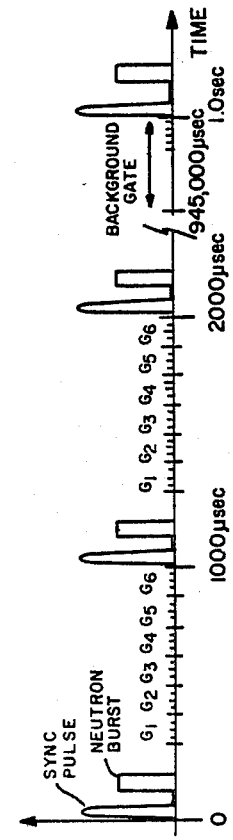
FIG. 6 is a schematic representation of a telemetry sequence as a function of time for the gating arrangement of FIG. 5.

Referring now to FIGS. 5 and 6, an alternative time gating scheme which employs the techniques of the present invention is illustrated schematically. In FIG. 5, a neutron burst of 15 to 20 microseconds duration is shown, a 20–30 microsecond moderation time interval follows the burst and then a time gate labelled gate 1 is opened for a relatively short duration of time. A slightly wider or longer duration time gate 2 is used. Subsequent time gates 3, 4, 5 and 6 are each of longer duration than their predecessor in the time gating sequence. The aim of this time gating scheme is to statistically optimize the counting rates in each of the gates. As the composite thermal neutron population decay curve falls off, the successively wider time gates allow more counts to occur at the lower counting rate of the later time gates. The actual times contemplated for time gating schemes shown in FIGS. 3 and 5 are given in Tables 1 and 2 which follows: (In Tables 1 and 2 all times are measured with respect to the reference time=0 at the beginning of the neutron burst).

TABLE 1

| \multicolumn{4}{c}{TIME GATING SCHEME OF FIG. 3} |
| Gate No. | Start Time | Stop Time | Duration |
| --- | --- | --- | --- |
| 1 | 50μ sec. | 195μ sec. | 145μ sec. |
| 2 | 200μ sec. | 345μ sec. | 145μ sec. |

TABLE 1-continued

| TIME GATING SCHEME OF FIG. 3 | | | |
|---|---|---|---|
| Gate No. | Start Time | Stop Time | Duration |
| 3 | 350μ sec. | 495μ sec. | 145μ sec. |
| 4 | 500μ sec. | 645μ sec. | 145μ sec. |
| 5 | 650μ sec. | 795μ sec. | 145μ sec. |
| 6 | 800μ sec. | 945μ sec. | 145μ sec. |

TABLE 2

| TIME GATING SCHEME OF FIG. 5 | | | |
|---|---|---|---|
| Gate No. | Start Time | Stop Time | Duration |
| 1 | 60μ sec. | 90μ sec. | 30μ sec. |
| 2 | 90μ sec. | 140μ sec. | 50μ sec. |
| 3 | 140μ sec. | 200μ sec. | 60μ sec. |
| 4 | 200μ sec. | 300μ sec. | 100μ sec. |
| 5 | 300μ sec. | 500μ sec. | 200μ sec. |
| 6 | 500μ sec. | 998μ sec. | 448μ sec. |

The slight time lapses (5μ sec.) between the time gates of Table 1 are supplied to account for time necessary to shift the contents of a counter into a memory buffer in the downhole tool electronics to be described subsequently. Similar short intervals would be required for the time gates of Table 2 but are omitted from the table for simplicity. It will be understood that it is meant to have the time gates of Tables 1 and 2 as nearly contiguous in time as is possible within the timing limitations of the electronics.

FIG. 6 illustrates a telemetry stream resulting from the time gating arrangement illustrated in FIG. 5. A synchronization pulse is sent to the surface by the downhole electronics. This is followed by the neutron burst and the reference time begins at the ending of the neutron burst. The short 10–30 microsecond moderation time interval elapses and then a digital number representing the counts made in time gate 1, labelled $G_1$ in FIG. 6, are telemetered to the surface. Similarly, digital numbers representing the counts in gates 2–6. This sequence is followed for 945 milliseconds. Then the background gating interval of 50 milliseconds is initiated as illustrated previously with respect to FIG. 4. In either event, the counting rates $C(t_i)$ i=1–6 are telemetered to the surface where they are employed in a surface computer (to be described in more detail subsequently) to employ a least-square fitting technique for extracting the parameters of interest.

Since Equation 4 is non-linear it is necessary to use an iterative fitting procedure for the least-squares fit. A particular fitting procedure is illustrated subsequently and will be described in more detail with respect to FIG. 7. It will suffice to say, however, at this point that the parameters of interest are obtained from the surface computer by a least-square iterative fitting procedure. The values of $\tau_F$, $\tau_B$, A, and B may then be recorded as a function of borehole depth in a conventional manner.

Referring now to FIG. 1, a well logging system in accordance with the concepts of the present invention is illustrated schematically. A well borehole 10 is filled with a borehole fluid 11 and penetrates earth formations 20 to be investigated. A downhole well logging sonde 12 is suspended in the borehole 10 via a conventional armored logging cable 13, in a manner known in the art, such that the sonde 12 maybe raised and lowered through the borehole as desired. The well logging cable 13 passes over a sheave wheel 14 at the surface. The sheave wheel 14 is electrically or mechanically coupled, as indicated by dotted line 15, to a well logging recorder 18 which may comprise an optical recorder, or magnetic tape, or both, as known in the art. The record of measurements made by the downhole sonde 12, may thus be recorded as a function of the depth in the borehole of the sonde 12.

In the downhole sonde 12, a neutron generator 21 is supplied with high voltage (approximately 100 kilovolts) for its operation by a high voltage power supply 22. Control and telemetry electronics 25 are utilized to supply control signals to the high voltage supply and the neutron generator 21 and to telemeter information measured by the downhole instrument to the surface via the logging cable 13.

Longitudinally spaced from the neutron generator 21 are two radiation detectors 23 and 24. Radiations detectors 23 and 24 may comprise, for example, thallium activated sodium iodide crystals which are optically coupled to photomultiplier tubes. The detectors 23 and 24 serve to detect gamma radiation produced in the surrounding formations 20 resulting from the action of the neutron generator 21 in emitting neutrons. A neutron shielding material 28 having a high density matter content or large scattering cross-section is interposed between the neutron generator 21 and the dual spaced detectors 23 and 24, in order to prevent direct irradiation of the detectors by neutrons emitted by the neutron generator 21. Shielding 29 may also be interposed between the detectors 23 and 24 if desired.

Upon activation of the neutron generator 21, a burst, or pulse, of neutrons of approximately 10–30 microseconds duration is initiated and is emitted into the well borehole 10, borehole fluid 11 and through the steel casing 26 and cement layer 27 surrounding the steel casing into earth formations 20 being investigated. The neutron burst is moderated or slowed down by scattering interactions such that the neutrons, are all essentially at thermal energy. The thermalized or thermal neutrons then begin capture interactions with the elemental nuclei of constituents of the earth formations 20 and pore spaces contained therein.

The capture of neutrons by nuclei of elements comprising the earth formations 20 and their pore spaces produce capture gamma rays which are emitted and impinge upon detectors 23 and 24. A voltage pulse is produced from the photomultipliers of detectors 23 and 24 for each gamma ray so detected. These voltage pulses are supplied to the electronics section 25, counted in a digital counter, and are telemetered to the surface via a conductor 16 of the well logging cable 13. At the surface, a surface electronics package 17 detects the telemetered information from the down hole sonde 12 and performs the least-squares fitting technique to determine the $\tau_F$, $\tau_B$, A and B with respect to the earth formations 20 being investigated. The surface electronics then supplies signals representative of the measured quantities to the recorder 18 where they are recorded as a function of borehole depth.

Figure 2:
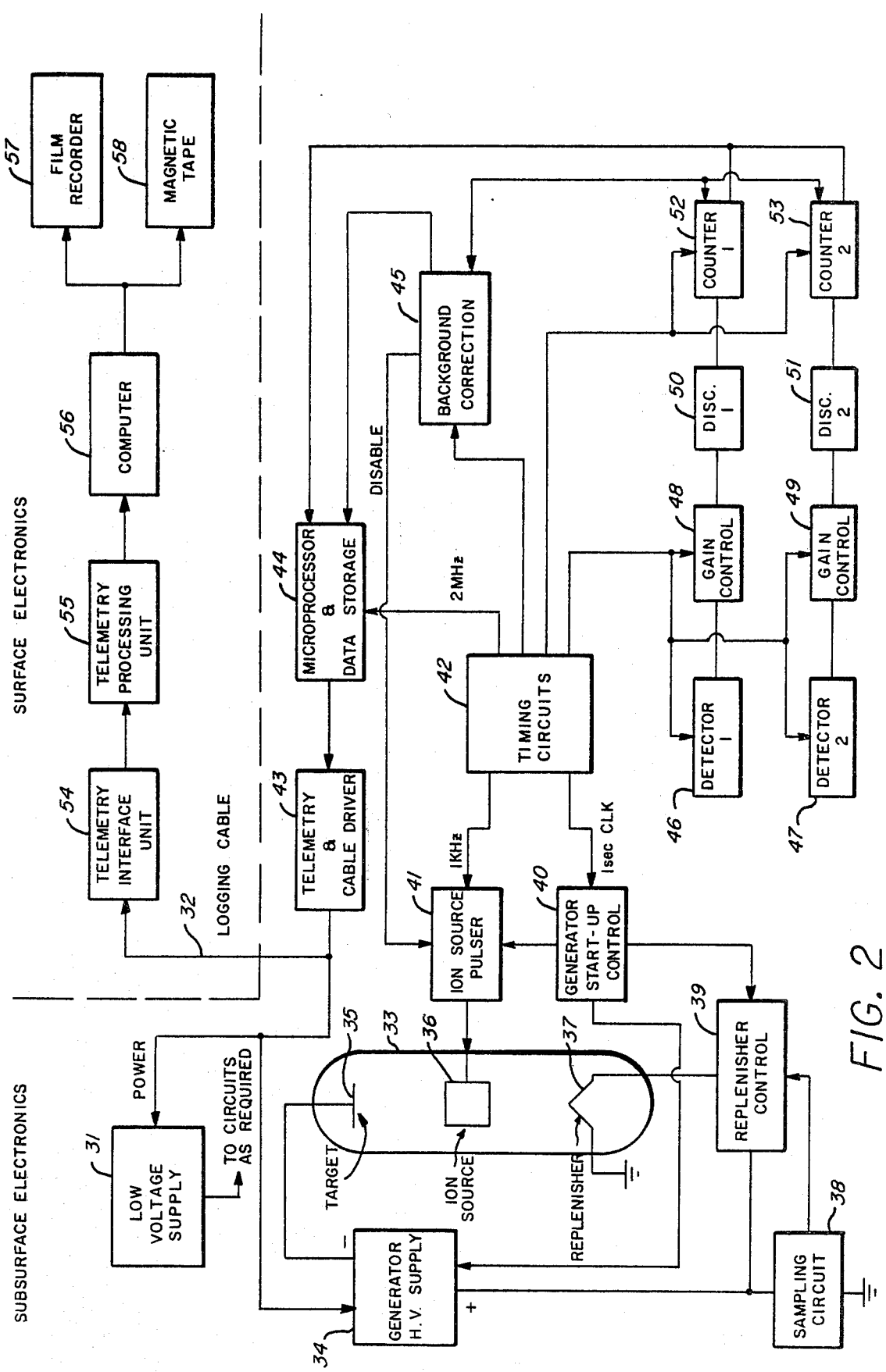
FIG. 2 is a schematic block diagram depicting the electronic systems of the well logging system of the present invention.

Referring now to FIG. 2, a schematic block diagram illustrating the electronic portions of the subsurface and surface electronic systems are illustrated in more detail but still schematically. Power for operation of the subsurface electronics is supplied via a conductor of the well logging cable 32 to a conventional low voltage power supply 31 and a high voltage power supply 34. The high voltage power supply 34 may be of the Cockcroft Walton multiple stage type and supplies approximately, 100 kilovolts for the operation of the neutron generator tube 33. The neutron generator tube 33 is of the deuterium-tritium accelerator type. An ion source 36 which is maintained at a potential near ground is used to generate deuterium-ions from deuterium gas filling the envelope of tube 33. A replenisher heater 37 is impregnated with additional deuterium and maintains a pressure level of deuterium gas inside the tube 33 envelope sufficient to supply ion source 36 with deuterium gas for ionization. A target 35 is impregnated with tritium and is maintained at a relatively high negative 100 kilovolts potential. The ion source is controlled by an ion source pulser 41. When supplied with a relatively low level voltage pulse, the ion source causes gas in the tube 33 envelope to become ionized and accelerated toward the target material 35. Upon impinging on the target material of target 35, the deuterium ions interact thermonuclearly with the tritium ions in the target to produce neutrons, which then are emitted in a generally spherically symmetrical fashion from the neutron generator tube 33 into the borehole and surrounding earth formations.

A replenisher control circuit 39 is supplied with samples of the neutron generator target current by a sampling circuit 38 and utilizes this to compare with a reference signal to control the replenisher current and thereby the gas pressure in the envelope of the neutron generator tube 33. Timing circuits 42 which comprise a master timing oscillator operating at a relatively high frequency and an appropriate divider chain, supplies 1 kilo hertz pulses to the ion source pulser 41, and also supplies one second clock pulses to the neutron generator start-up control circuit 40. Moreover, timing circuit 42 supplies 2 mega hertz clock pulses to a microprocessor and data storage array 44 and supplies timing pulses to the background circuit 45 and counters 52 and 53. Similarly, timing signals are supplied to a pair of gain control circuits 48 and 49.

The interaction of thermalized neutrons with nuclei of earth formation materials causes the emission of capture gamma rays which are detected by detectors 46 and 47 (corresponding to the dual spaced detectors 23 and 24 of FIG. 1). Voltage pulses from the detectors 46 and 47 are supplied to gain control circuits 48 and 49 respectively. Gain control circuits 48 and 49 serve to maintain the pulse height output of detectors 46 and 47 in a calibrated manner with respect to a known amplitude reference pulse. Output signals from the gain control circuits corresponding to gamma rays detected by detectors 46 and 47 are supplied to discriminator circuits 50 and 51 respectively. The discriminator circuits 50 and 51 serve to prevent low amplitude voltage pulses from the detectors from entering counters 52 and 53. Typically, the discriminators are set at about 0.1–0.5 Mev to eliminate noise generated by the photomultiplier tubes associated with detectors 46 and 47. The discriminator 50 and 51 outputs are supplied to counters 52 and 53 which serve to count individual capture gamma ray events detected by the detectors 46 and 47. Outputs from the counters 52 and 53 are supplied to the microprocessor and data storage circuits 44.

During the background portion of the detection cycle the background circuit 45 is supplied with counts from the counters 52 and 53. This circuit also provides a disable pulse to the ion source 41 to prevent pulsing of the neutron generator during the background counting portion of the cycle. The background correction circuit 45 supplies background count information to microprocessor and data storage 44. Background may be stored and averaged for longer periods than capture data since at low discriminator threshold, most background is from gamma ray (NaI,) activation which has 27 minutes half life. Better statistics in substracted signal results.

The digital count information from counters 52 and 53 and background correction circuit 45 are supplied to the microprocessor and data storage circuit 44. These circuits 44 format the data and present it in a serial manner to the telemetry circuit 43 which is used to telemeter the digital information from the counters and background correction circuit to the surface via well logging cable 32. At the surface, a telemetry interface unit 54 detects the analog telemetry voltage signals from the logging cable 32 conductors and supplies them to a telemetry processing unit 55 which formats the digital count rate information representing the counting rate from counters 52 and 53 in the subsurface equipment in terms of the time gating schemes as previously discussed. The digital numbers representative of the count rates in each of the six or more time gates and the background counting rate are then supplied to a digital computer 56.

Figure 7:
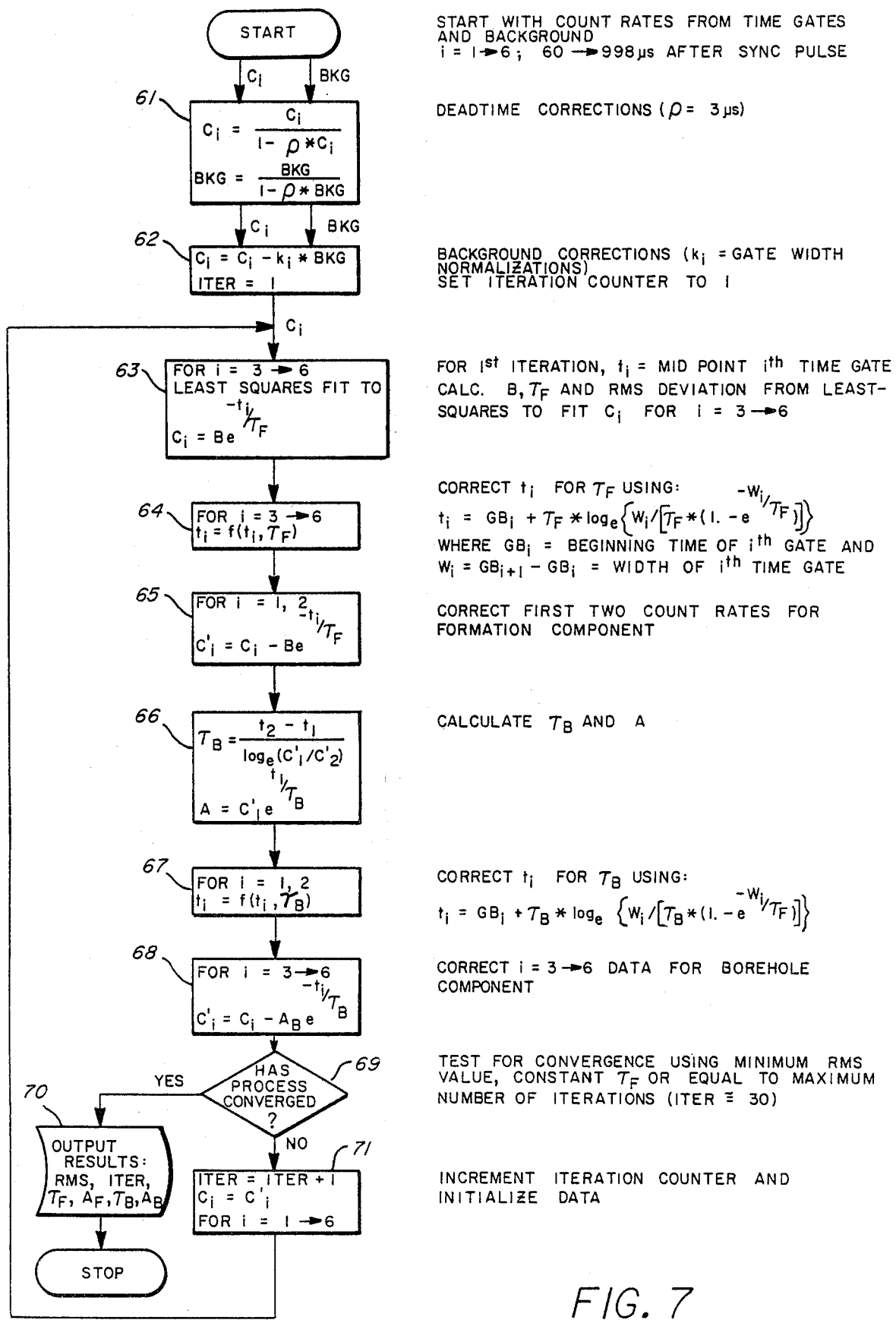
FIG. 7 is a flow chart diagram illustrating an embodiment of one method for obtaining parameters of interest of earth formations by a surface computer.

The computer 56 is programmed in accordance with the flow chart of FIG. 7 to interpret the six or more time gates and background counting rate information in terms of the thermal neutron decay or thermal neutron lifetime of the borehole and formation components. Output signals representing formation parameters of interest are supplied from the computer 56 to a film recorder 57 and a magnetic tape recorder 58 for recording as a function of borehole depth. The surface computer 56 is programmed in accordance with the flow chart illustrated in FIG. 7 to extract the earth formation and borehole components of thermal neutron decay time $\tau_F$ and $\tau_B$ and the intercepts B and A of FIG. 3 which represent the counting rates at the end of the neutron burst due to the formation and borehole components of thermal neutron population respectively. In order to accomplish this an iterative least squares fitting scheme is illustrated in FIG. 7 is utilized.

Input information to the program illustrated in FIG. 7 comprises counting rate information $C_i$, i=1,6 from each of the six time gates and a background count labelled BKG in FIG. 7. At a first control block 61, the counting rates from each of the time gates are corrected for dead time in the detectors by a formula illustrated in block 61. Additionally, the background counts are corrected for this dead time. The corrected count rate information and background information are supplied to program control block 62 where the background count rate is normalized to take into account the different durations of the time gates 1–6. The background count is converted to background count rate and subtraced from the count rate information in each time gate.

The corrected for background count rates, $C_i$, are then supplied to a program control block 63 assuming $t_i$ to be the mid point of each time gate. The count rate data $C_i$, for i=3–6, is then least-squares fitted to the expression given in block 63, resulting in preliminary values of B, $\tau_F$ and the RMS derivation from the least-squares fit to the count rates for each value of count rate.

The estimates of $t_i$ are then supplied to a program control block 64 in which the $t_i$ corresponding to the center of the time gate is corrected for the slope of the formation thermal neutron decay time $\tau_F$ via an expression illustrated in block 64. Similarly, the count rate information $C_i$ for the first two time gates i=1,2 which is more effected by the borehole component is corrected for the effect due to the formation component $\tau_F$ in a program control block 65.

The corrected counting rates $C'_i$, i=1,6 are then supplied to a program control block 66 which calculates a borehole component of thermal neutron decay time $\tau_B$ and borehole component count rate amplitude component A, according to expressions given in program control block 66.

The center time coordinate for gates 1 and 2 is then corrected for the slope of the borehole component $\tau_B$ according to the expression given in block 67.

Control is then transferred to a program control block 68 where the expression for the counting rate $C_i$, i=3-6 in time gates 3-6 are corrected for borehole component according to the expression given in block 68.

Control is then transferred to program control block 69 where a test is performed to determine if the iterative process has converged. If convergence has not been achieved as determined by the test at block 69, then an iteration counter is incremented at block 71 and the corrected count rate data $C'_i$, i=1,6 as determined in program control block 68 and 65 is substituted for the previous count rate data from the last iteration and the program loops backs to program control block 63 for the next iteration of least-squares fitting. When convergance has been achieved as determined by the test at block 69, then output block 70 is entered and the results output to the recorders illustrated in FIG. 2 from the control computer 56 of FIG. 2.

In this manner, the system of the present invention simultaneously measures the thermal neutron decay time of the earth formation component $\tau_F$, the borehole component $\tau_B$ and the initial count rates amplitudes B and A due to formation and borehole components of count rate. All of the previously mentioned limitations of the prior art made by assuming the borehole component of thermal neutron decay time to be much smaller than the formation component in prior art techniques are thereby avoided.

The foregoing descriptions may make other alternative embodiments of the present invention apparent to those skilled in the art. It is therefore, the aim of the appended claims to cover all such changes and modifications as fall within the true spirit and scope of the invention.

We claim:

1. A method for simultaneously measuring the thermal neutron decay time of materials in and about a well borehole, comprising the steps of:
   generating, in a well borehole, a relatively short duration discrete burst of fast neutrons which are rapidly moderated by interaction with nuclei of materials in the borehole and surrounding earth formations and slowed down to thermal energy, creating a thermal neutron population in the borehole and surrounding earth formations;
   detecting, in the borehole, radiations representative of the thermal neutron population in the borehole and surrounding earth formations, in at least four time intervals subsequent to said burst of fast neutrons and generating, at least four count signals representative of said thermal neutron population during said at least four time intervals; and
   combining said at least four count signals according to a predetermined relationship to simultaneously separate the borehole and formation decay components and to derive at least two measurement signals representative of the thermal neutron decay time of the borehole medium and the earth formation medium in the vicinity of the borehole.

2. The method of claim 1 and further including the step of, in the step of combining said at least four count signals according to a predetermined relationship, simultaneously deriving at least two additional measurement signals representative of the initial thermal neutron population in the borehole and in the media surrounding the borehole.

3. The method of claim 1 wherein the detecting step is performed by detecting gamma radiations resulting from the capture of thermal neutrons by nuclei of materials in and about the borehole.

4. The method of claim 3 wherein said detecting step includes detecting said gamma radiations in at least six time intervals subsequent to said burst of fast neutrons.

5. The method of claim 1 wherein said detecting step is initiated approximately 20 to 50 microseconds subsequent to said neutron burst to allow neutron moderation in the borehole and formations and said at least four time intervals extend substantially for a total duration of approximately one millisecond, subsequent to said neutron burst.

6. The method of claim 5 wherein said at least four time intervals are of approximately equal duration.

7. The method of claim 5 wherein said at least four time intervals are each of successively greater duration, so as to optimize the total count in each such time interval.

8. The method of claim 1 wherein said generating step is performed using a source of approximately 14 MEV neutron generated by a deuterium-tritium type accelerator tube.

9. The method of claim 1 and further including the step of, subsequent to said step of detecting in at least four time intervals subsequent to said burst of fast neutrons, detecting background radiations in the well borehole and correcting said at least four count signals for said background radiations prior to said combining step.

10. The method of claim 9 wherein the background correction is performed by subtracting a weighted function of said detected background radiations from each of said at least four count signals.

11. A method for simultaneously determining the borehole component and the formation component of thermal neutron decay time of a borehole and earth formations in the vicinity of the borehole, comprising the steps of:
    repetitively emitting, in a well borehole, relatively short duration pulses of fast neutrons which are rapidly moderated by interaction with nuclei of materials in the borehole and surrounding earth formations and slowed down to thermal energy, creating repetitive bursts of thermal neutron populations in the borehole and surrounding earth formations;
    detecting, in the borehole during a time interval between said repetitive pulses of fast neutrons, radiations representative of the thermal neutron population in the borehole and surrounding earth formations, in at least four time intervals subsequent to a pulse of fast neutrons and generating at least four count signals representative of said thermal neutron population during said at least four time intervals;

suppressing a plurality of said repetitive neutron pulses;

detecting, during a separate time interval between said repetitive pulses, and while said pulses are suppressed, radiations attributable to a background radiation component of radiation in the borehole and generating a background count signal representative thereof;

combining said at least four count signals and a function of said background count signal according to a predetermined relationship to simultaneously separate the borehole and formation decay components and to derive at least two measurement signals representative of the thermal neutron decay times of said borehole component and said formation component; and recording said at least two measurement signals as a function of borehole depth.

12. The method of claim 11 wherein each of the steps is performed at a plurality of different depths in a well borehole and a recording of said at least two measurement signals is made for each of said plurality of depths in the borehole.

13. The method of claim 11 wherein said emitting and detecting steps are repeated approximately 1000 times per second.

14. The method of claim 11 and further including in the step of combining said at least four count signals according to a predetermined relationship, simultaneously deriving at least two additional measurement signals representative of the initial thermal neutron population following a repetitive neutron pulse in the borehole and in the media surrounding the borehole.

15. The method of claim 11 wherein the detecting steps are performed by detecting gamma radiations resulting from the capture of thermal neutrons by the nuclei of materials within and without the borehole.

16. The method of claim 15 wherein said detecting steps include detecting said gamma radiations in at least six time intervals subsequent to each burst of fast neutrons and generating at least six count signals representative thereof.

17. The method of claim 11 wherein said detecting steps are initiated approximately 20 to 50 microseconds subsequent to each such neutron burst to allow neutron moderation in the borehole and formations and said at least four time intervals extend substantially over the entire time interval until the next of said repetitive neutron pulses.

18. The method of claim 17 wherein said at least four time intervals are of approximately equal duration.

19. The method of claim 17 wherein said at least four time intervals are each of successively greater duration, so as to optimize the total count in each such time interval.

20. The method of claim 11 wherein said generating step is performed using a source of approximately 14 MEV neutrons generated by a deuterium-tritium type accelerator tube.

21. The method of claim 11 wherein said combining step includes subtracting a weighted function of said detected background radiation from each of said at least four count rate signals.

* * * * *